(12) United States Patent
Thomas et al.

(10) Patent No.: US 8,088,091 B2
(45) Date of Patent: Jan. 3, 2012

(54) NO CLOG SHUNT USING A COMPACT FLUID DRAG PATH

(75) Inventors: Gordon A. Thomas, Princeton, NJ (US); Reginald Conway Farrow, Somerset, NJ (US); Sheng Liu, Harrison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 181 days.

(21) Appl. No.: 12/381,170

(22) Filed: Mar. 9, 2009

(65) Prior Publication Data

US 2010/0228179 A1    Sep. 9, 2010

(51) Int. Cl.
*A61M 1/00* (2006.01)
*A61M 5/00* (2006.01)

(52) U.S. Cl. .................. 604/9; 604/8; 604/540
(58) Field of Classification Search .................. 604/9, 8, 604/540; 606/200
See application file for complete search history.

(56) References Cited

U.S. PATENT DOCUMENTS

| | | |
|---|---|---|
| 2,718,144 A | 9/1955 | Hornfeck |
| 3,017,885 A | 1/1962 | Robicsek |
| 3,409,763 A | 11/1968 | Schoppe, Jr. |
| 3,669,116 A | 6/1972 | Heyer |
| 3,847,020 A | 11/1974 | Jurschak |
| 3,960,143 A | 6/1976 | Terada |
| 4,377,169 A | 3/1983 | Banks |
| 4,382,445 A | 5/1983 | Sommers |
| 4,385,636 A | 5/1983 | Cosman |
| 4,581,943 A | 4/1986 | Feller |
| 4,588,085 A | 5/1986 | Sussman |
| 4,593,703 A | 6/1986 | Cosman |
| 4,605,395 A | 8/1986 | Rose |
| 4,741,730 A | 5/1988 | Dormandy |
| 4,931,039 A | 6/1990 | Coe |
| 5,000,731 A | 3/1991 | Wong |
| 5,038,773 A | 8/1991 | Norlien |
| 5,069,674 A * | 12/1991 | Fearnot et al. ................ 604/524 |
| 5,207,684 A | 5/1993 | Nobles |
| 5,304,114 A | 4/1994 | Cosman |
| 5,535,633 A | 7/1996 | Kofoed et al. |
| 5,728,061 A | 3/1998 | Ahmed |
| 5,772,625 A | 6/1998 | Krueger |
| 5,928,182 A | 7/1999 | Kraus |
| 5,980,480 A | 11/1999 | Rubenstein |
| 6,053,873 A | 4/2000 | Govari |
| 6,085,599 A | 7/2000 | Feller |
| 6,264,625 B1 | 7/2001 | Rubenstein |
| 6,432,050 B1 | 8/2002 | Porat |
| 6,585,677 B2 | 7/2003 | Cowan, Jr. |
| 6,689,085 B1 | 2/2004 | Rubenstein |
| 6,840,917 B2 | 1/2005 | Marion |
| 6,875,192 B1 | 4/2005 | Saul |
| 6,905,474 B2 | 6/2005 | Borgesen |

(Continued)

FOREIGN PATENT DOCUMENTS

EP     0 888 795     1/1999

(Continued)

*Primary Examiner* — Melanie Hand
(74) *Attorney, Agent, or Firm* — Gearhart Law, LLC

(57) ABSTRACT

The present invention is an improved shunt system for draining CSF. The system includes a removable sheath for reduction of catheter clogging during shunt insertion, a catheter with relatively large holes, an extracranial filter to allow non-invasive filter replacement, and a wireless flow/pressure meter to monitor and control CSF flow.

14 Claims, 5 Drawing Sheets

U.S. PATENT DOCUMENTS

| | | |
|---|---|---|
| 6,926,691 B2 | 8/2005 | Miethke |
| 7,025,742 B2 | 4/2006 | Rubenstein |
| 7,037,288 B2 | 5/2006 | Rosenberg |
| 7,041,083 B2 | 5/2006 | Chu |
| 7,118,548 B2 | 10/2006 | Borgesen |
| 7,290,454 B2 | 11/2007 | Liu |
| 7,337,678 B2 | 3/2008 | Thakre |
| 2002/0123714 A1 | 9/2002 | Saul |
| 2003/0032915 A1 | 2/2003 | Saul |
| 2003/0045870 A1 | 3/2003 | Madsen |
| 2003/0135147 A1 | 7/2003 | Rosenberg |
| 2003/0159697 A1 | 8/2003 | Wallace |
| 2004/0030279 A1 | 2/2004 | Rubenstein |
| 2004/0068201 A1 | 4/2004 | Saul |
| 2004/0092908 A1 | 5/2004 | Harper |
| 2004/0092909 A1 | 5/2004 | Harper |
| 2004/0102761 A1 | 5/2004 | Ahmed |
| 2004/0122348 A1 | 6/2004 | Hokanson |
| 2004/0147871 A1 | 7/2004 | Burnett |
| 2004/0215067 A1 | 10/2004 | Stiger |
| 2004/0236309 A1 | 11/2004 | Yang |
| 2004/0243192 A1* | 12/2004 | Hepp et al. ............ 607/17 |
| 2004/0260229 A1 | 12/2004 | Meir |
| 2004/0267187 A1 | 12/2004 | Rosenberg |
| 2005/0055009 A1 | 3/2005 | Rosenberg |
| 2005/0085764 A1 | 4/2005 | Borgesen |
| 2005/0085841 A1* | 4/2005 | Eversull et al. ............ 606/190 |
| 2005/0096582 A1 | 5/2005 | Burnett |
| 2005/0113802 A1 | 5/2005 | Watson |
| 2005/0267413 A1 | 12/2005 | Wang |
| 2006/0151923 A1 | 7/2006 | Wilkowske et al. |
| 2006/0228453 A1 | 10/2006 | Cromack et al. |
| 2007/0038171 A1 | 2/2007 | Mayer |
| 2007/0131279 A1 | 6/2007 | Thakre |
| 2007/0225687 A1* | 9/2007 | House ............ 604/544 |
| 2007/0261496 A1 | 11/2007 | Jonsson |
| 2008/0065008 A1* | 3/2008 | Barbut et al. ............ 604/96.01 |
| 2008/0208245 A1* | 8/2008 | Hoffman ............ 606/200 |

FOREIGN PATENT DOCUMENTS

| | | |
|---|---|---|
| EP | 0 904 728 | 3/1999 |
| EP | 0 904 728 A2 | 3/1999 |
| EP | 0 921 836 | 6/1999 |
| EP | 1 007 113 | 6/2000 |
| EP | 1 050 264 | 11/2000 |
| EP | 683890 | 4/2002 |
| EP | 745213 | 9/2002 |
| EP | 1 327 459 | 7/2003 |
| EP | 1 512 428 | 9/2003 |
| EP | 1 491 137 | 12/2004 |
| EP | 1 491 137 | 3/2005 |
| EP | 1 552 784 | 7/2005 |
| EP | 0 904 728 B1 | 11/2005 |
| GB | 1271361 | 4/1972 |
| WO | WO/83/01387 | 4/1983 |
| WO | WO/87/02255 | 4/1987 |
| WO | WO/91/17779 | 11/1991 |
| WO | WO/95/19549 | 7/1995 |
| WO | WO/98/02202 | 1/1998 |
| WO | WO/98/18510 | 5/1998 |
| WO | WO/98/30275 | 7/1998 |
| WO | WO/99/53990 | 10/1999 |
| WO | WO/01/36014 | 5/2001 |
| WO | WO/2004/073768 | 9/2004 |
| WO | WO/2006/009467 | 1/2006 |
| WO | WO/2007/015934 | 2/2007 |
| WO | WO/2007/075349 | 7/2007 |
| WO | WO/2007/127305 | 11/2007 |
| WO | WO/2007/127619 | 11/2007 |
| WO | WO/2008/005440 | 1/2008 |
| WO | WO/2008/027322 | 3/2008 |

* cited by examiner

NO CLOG SHUNT USING A COMPACT FLUID DRAG PATH

FIELD OF THE INVENTION

The present invention relates to medical devices, more specifically to a fluid management device or shunt, that minimizes the risk of blockage or obstruction of pores in the catheter and which contains a pressure and flow control meter.

BACKGROUND OF THE INVENTION

Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. Because CSF keeps the brain and spinal cord buoyant, it acts as a protective cushion or "shock absorber" to prevent injuries to the central nervous system.

Hydrocephalus, which affects children and adults, arises when the normal drainage of CSF in the brain is blocked in some way. Such blockage can be caused by a number of factors, including, for example, genetic predisposition, intraventricular or intracranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure on the brain, which causes the ventricles to enlarge.

Hydrocephalus is most often treated by surgically inserting a shunt system that diverts the flow of CSF from the ventricle to another area of the body where the CSF can be absorbed as part of the circulatory system. Shunt systems come in a variety of models, and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The ventricular catheter typically contains multiple holes or pores positioned along the length of the ventricular catheter to allow the CSF to enter into the shunt system. To facilitate catheter insertion, a removable rigid stylet, situated within the lumen of the ventricular catheter, is used to direct the catheter toward the desired targeted location. Alternatively, or in addition, blunt tip brain cannulas and peel-away sheaths have been used to aid placement of the catheters.

Shunting is considered one of the basic neurosurgical procedures, yet it has the highest complication rate. The most common complication with shunting is obstruction of the system. Although obstruction or clogging may occur at any point along the shunt system, it most frequently occurs at the ventricular end of the shunt system. While there are several ways that the ventricular catheter may become blocked or clogged, obstruction is typically caused by growth of tissue, such as the choroid plexus, around the catheter and into the pores. The pores of the ventricular catheter can also be obstructed by debris, bacteria, or blood clogged in the pores of the catheter. Additionally, problems with the ventricular catheter can arise from overdrainage of the CSF, which can cause the ventricle walls to collapse upon the catheter and block the pores in the catheter wall, thereby preventing CSF drainage.

Some of these problems can be treated by backflushing, which is a process that uses the CSF present in the shunt system to remove the obstructing matter. This process can be ineffective, however, due to the small size of the pores of the ventricular catheter and due to the small amount of flushing liquid available in the shunt system. Other shunt systems have been designed to include a mechanism for flushing the shunt system. For example, some shunt systems include a pumping device within the system which causes fluid in the system to flow with considerable pressure and velocity, thereby flushing the system. As with the process of backflushing, using a built-in mechanism to flush the shunt system can also fail to remove the obstruction due to factors such as the size of the pores and the degree and extent to which the pores have been clogged.

Occluded ventricular catheters can also be repaired by cauterizing the catheter to remove blocking tissue, thereby reopening existing pores that have become occluded. Alternatively, new pores can be created in the catheter. These repairs, however, may be incapable of removing obstructions from the ventricular catheter depending on the location of the clogged pores. Additionally, the extent of tissue growth into and around the catheter can also preclude the creation of additional pores, for example, in situations where the tissue growth covers a substantial portion of the ventricular catheter. Another disadvantage of creating new apertures to repair an occluded ventricular catheter is that this method fails to prevent or reduce the risk of repeated obstructions.

Because attempts at flushing or repairing a blocked ventricular catheter are often futile and ineffective, occlusion is more often treated by replacing the catheter. Although this can be accomplished by simply removing the obstructed catheter from the ventricle, the growth of the choroid plexus and other tissues around the catheter and into the pores can hinder removal and replacement of the catheter. Care must be exercised to avoid damage to the choroid plexus, which can cause severe injury to the patient, such as, for example, hemorrhaging. Not only do these procedures pose a significant risk of injury to the patient, they can also be very costly, especially when shunt obstruction is a recurring problem.

Accordingly, there exists a need for a shunt system that minimizes or eliminates the risk of blockage or obstruction of the catheter pores, and reduces the need for repeated repair and/or replacement, while maintaining the proper CSF level in the brain. Attempts have been made to solve the problems inherent in the shunting process. Some of the prior art is described below.

U.S. Pat. No. 3,669,116 teaches a physiological drainage catheter comprising an elongated tube with a central axis and a peripheral wall surrounding it. A port passes through the wall to the passage for the purpose of draining fluid from the region surrounding the tube. A peripheral cuff surrounds the wall and is fastened thereto on each side of the port, the cuff ballooning away from the wall to leave a cavity therebetween. The cuff is made of a flexible openpore silicone rubber sponge which provides a large number of restricted, but continuous, passages from outside of the cuff to the cavity, and an increased surface area thereby to screen or filter fluid which reaches the port from regions to be drained outside the cuff to minimize clogging, and by its increased surface area to decrease the possibility of being closed by abutment with surrounding tissue.

U.S. Pat. No. 4,593,703 teaches an improvement in design of an implantable telemetric differential pressure sensing device enabling thinner, more compact, and simplified construction for the device; increased pressure sensitivity and range of measurement; and a wider class of applications for such pressure sensing devices in diagnostic medicine and clinical monitoring. The implanted device includes a thin, planar, closed, conductive loop which moves with a flexible diaphragm, the diaphragm moving upon changes in the difference of two bodily pressures on its opposite sides. The position of the conductive loop relative to a resonant circuit fixed in the device determines the resonant frequency of the resonant circuit. The resonant frequency is detected telemetrically outside the body, and its value is used to determine the difference in the two bodily pressures U.S. Pat. No. 7,025,742 teaches a method that treats a patient for adult-onset dementia of the Alzheimer's type by removing a portion of the patient's cerebrospinal fluid, preferably (although not necessarily) by transporting the fluid to another portion of the patient's body. An apparatus for removing cerebrospinal fluid includes (1) a conduit with a first opening and a second opening, the first opening of the conduit being disposed in fluid communication with a space within a patient's subarachnoid space, the second opening being disposed in fluid communication with another portion of the patient's body; and (2) a flow rate control device attached to the conduit.

U.S. Pat. No. 7,290,454 teaches a differential pressure flow sensor system comprising a disposable flow sensor which has upstream and downstream pressure sensing devices for detecting a differential pressure in a flow channel. Each sensing device comprises a diaphragm, a capacitor and an inductor electrically coupled to the capacitor so as to form an LC tank circuit. The capacitor and/or inductor can be mechanically coupled to the diaphragm such that a deflection of the diaphragm in response to fluid pressure applied thereto causes a change in the resonant frequency of the LC tank. The differential pressure and flow rate can be determined by detecting changes in the resonant frequency using interrogation electronics which can wirelessly interrogate the devices. A calibration capacitor and/or inductor can be formed on each sensing device and trimmed thereon for calibration purposes. Such pressure flow systems can be implemented in medical applications.

US Application 200401487871 teaches an implantable fluid management device, designed to drain excess fluid from a variety of locations in a living host into a second location within the host, such as the bladder of that host. The device may be used to treat ascites, chronic pericardial effusions, normopressure hydrocephalus, hydrocephalus, pulmonary edema, or any fluid collection within the body of a human, or a non-human mammal.

US Application 20040260229 and International Patent Application EP 1491137 teach an implantable medical device that includes a housing, a valve disposed within the housing, a first pressure sensor disposed within the housing upstream of the valve, and a second pressure sensor disposed within the housing downstream of the valve. A CPU is disposed within the housing and is electrically connected to the first pressure sensor and the second pressure sensor. To communicate the measured pressure information to an external device, the CPU compares the pressure measured by the first pressure sensor to the pressure measured by the second pressure sensor and wirelessly communicates these compared pressures to an external device. Alternatively, the CPU may wirelessly communicate the absolute value of the pressure measured by the first pressure sensor and the second pressure sensor to the external device. Additionally, the CPU and sensors may be non-invasively powered using optical or acoustical methods.

US Application 20050113802 teaches a surgically implantable delivery or drainage catheter assembly that includes a porous fiber membrane that is permeable to the intended drainage or delivery fluid, yet has an outer surface morphology and porosity that prevents the ingrowth of tissue. The porous fiber membrane is created using a phase-inversion process which is controlled to select a desired porosity. A reinforcement member is also disposed within the porous fiber membrane.

US Application 20070261496 teaches a biological fluid device that comprises a pressure sensor, which is arranged on the device. The pressure sensor comprises a compressible container, the compression of which is indicative of the pressure, and is capable of wireless communication.

International Patent Application WO/2004/073768 teaches an occlusion resistant medical shunt, particularly a hydrocephalic shunt, that is provided for implantation into a mammal. The shunt has an elongate wall structure configured as a tube having a lumen therethrough and a proximal end for receipt of bodily fluids. The bodily fluids, such as cerebrospinal fluid, flows through the shunt to a distal end for discharge of the bodily fluids. The wall structure of the shunt generally includes a biocompatible medical device material. The shunts of the present invention further include one or more occlusion resistant materials to resist occlusion of the lumenal passage in the shunt.

International Patent Application WO/2006/009467 describes a method for processing pressure signals derived from locations inside or outside a human or animal body or body cavity. Different aspects of the invention relate to a method for optimal differentiating between cardiac beat- and artifact-induced pressure waves, a method for obtaining new and improved information from said pressure signals, and method(s) for predicting pressures inside a body or body cavity from pressure-related signals derivable from outside said body or body cavity. The invention also relates to device(s) and system for sensing continuous pressures signals and displaying output of processing according to the inventive method. Other features of this invention are related to aspects of draining fluid from a brain or spinal fluid cavity.

International Patent Application WO/2007/075349 teaches a differential pressure flow sensor system that comprises a disposable flow sensor which has upstream and downstream pressure sensing devices for detecting a differential pressure in a flow channel. Each sensing device comprises a diaphragm, a capacitor and an inductor electrically coupled to the capacitor so as to form an LC tank circuit. The capacitor and/or inductor can be mechanically coupled to the diaphragm such that a deflection of the diaphragm in response to fluid pressure applied thereto causes a change in the resonant frequency of the LC tank. The differential pressure and flow rate can be determined by detecting changes in the resonant frequency using interrogation electronics which can wirelessly interrogate the devices. A calibration capacitor and/or inductor can be formed on each sensing device and trimmed thereon for calibration purposes. Such pressure flow systems can be implemented in medical applications.

British Patent GB1271361 teaches an apparatus for monitoring the flow of fluid past a surface that comprises a transducer associated with the surface to produce an electric signal representative of the pressure variations due to turbulence, which may be already existing or artificially promoted. For monitoring blood flow in a silastic tube forming part of a dialysis shunt between an artery and a vein, the tube sits in a stirrup part of a body attached by arm to a leaf-spring anchored at one end to a gramophone pick-up arm with a Piezo-electric stylus. The pressure variations in the tube due to turbulence are converted to electrical signals, which are fed to an amplifier and earphones and also rectified and fed to a Schmitt trigger circuit to operate an alarm when the flowrate falls below a predetermined value.

None of the prior art addresses the issues with shunting in as effective a manner as the current invention. The current invention employs three novel shunt technologies for controlling CSF coupled with a pressure/flow sensor that is wireless and implantable. The novel shunt technologies involve an insertion mechanism followed by a two-stage system for reduction of shunt clogging. In the insertion mechanism, the catheter is covered with a removable sheath that prevents clogging of the catheter holes on insertion. In one embodiment, the removable sheath is coated with a substance that will cause particles to adhere to the sheath. The coated sheath is left for an appropriate period of time after insertion of the catheter to remove the removable sheath, so that particulates may settle and the maximum removal effect may be achieved. In the two stage system, the CSF passes through catheter holes that are larger than in typical currently available shunt catheters, and in the second stage passes through a replaceable filter downstream. The current invention decreases invasiveness by employing the filter in an extracranial position, making it relatively easy to remove and replace, as well as easy to monitor and maintain. In addition, a wireless pressure/flow sensor is employed to control flow and CSF fluid levels. The flow sensor is immersible and exhibits reduced vulnerability to pressure and temperature changes and body orientation changes, making it more accurate than flow sensors that have been used in various shunt systems.

SUMMARY OF THE INVENTION

The present invention is a medical apparatus, consisting of a removable sheath, suitable for surrounding a catheter during insertion of the catheter into an organ, and a shunt tube with a tip having enlarged pores.

The redesigned shunt of the current invention includes the following features not present in the prior art:

A removable sheath that is coated or not coated with a layer to which particulates tend to adhere; the removable sheath is placed on the proximate (or ventricular) end of the shunt tube to be used during insertion. The removable sheath is removed after the disturbance due to insertion settles. This feature will keep the tube clear of obstructions during and immediately after insertion.

An increased pore opening size. The end of the shunt tube is opened to a standard shunt tube diameter of 1.0 to 1.3 mm, with added holes in the sides of comparable diameter so that particles with smaller diameter can enter without obstruction. The shunt tube is coated with a layer that has a low adhesion for the particulates from the ventricular brain cavity as are most current shunt tubes. The holes in the side of the tube are comparable to the tube diameter. This feature will allow particulates, except unlikely ones with diameters greater than 1.0 mm, to enter the tube, shifting particulate accumulation away from the ventricular region of the shunt which is the least convenient place and where there is no room for a large filter, to an extracranial location.

The use of a shunt with a shunt tube having a large capacity filter at an extracranial location for hydrocephalus. The filter is designed in the form of a large sheet through which water flows in from below and out above. In a preferred embodiment, the filter pore size is 0.3-0.4 mm diameter, small enough to eliminate particles that would clog other devices, such as pressure and back-flow control and pressure and flow measurement devices. The filter is placed subcutaneously, but at a convenient location for surgical access or is placed partially external to a patient's skin when the shunt is implanted. The filter resides in a housing, so that it may be easily removed without disturbing any other part of the system, especially the tubing that traverses the patient's body and connects to the housing. For instance, in the case of a filter for the eye, the filter may be accessible by raising the eyelid. The key is that the procedure would be much simpler and less prone to infection than a re-implantation of the entire shunt, which is the current standard procedure when a shunt clogs.

The shunt has an additional component, selected from the group consisting of: a pressure control, a backflow control, a pressure measurement device, a flow measurement device, or combinations thereof. The flow meter is a sensor suitable for placement under the skin of a human or animal, and has a first chamber, having a first inlet to allow the passage of a fluid into the first chamber, a first capacitor disposed in the first chamber capable of reacting to pressure created by the fluid, and a first inductor connected to the first capacitor; the first chamber further having an outlet connected to a channel that is in fluid communication with a second chamber; the second chamber having a second inlet to allow the passage of a fluid into the second chamber, a second capacitor disposed in the second chamber capable of reacting to pressure created by the fluid, and a second inductor connected to the second capacitor and an outlet to allow fluid to exit the sensor.

The flow meter and the filter together would allow an indication of partial clogging of the filter and a means of changing the filter just when change is needed.

It is an object of the invention to provide a shunt that exhibits reduced clogging because the proximal holes would be bigger and the distal holes would be more numerous compared to currently available shunts.

It is an object of the invention to provide a shunt that is inserted with a removable sheath.

It is an object of the invention to provide a removable sheath that is removed by tearing along a perforation or seam.

It is an object of the invention to provide a removable sheath that attracts particulate matter.

It is an object of the invention to provide a removable sheath that is plastic.

It is an object of the invention to provide a removable sheath that is paper or fiberglass.

It is an object of the invention to provide a catheter that has a tip and a plurality of holes.

It is an object of the invention to provide a catheter that is coated with a material having a low adhesion to particulate matter, as currently with all shunt tubes.

It is an object of the invention to provide a shunt system employing an extracranial filter.

It is an object of the invention to provide an extracranial filter with a filter component that is removable and replaceable with minimal invasion.

It is an object of the invention to provide an extracranial filter with a filter component that is replaceable without a minimally invasive procedure.

It is an object of the invention to provide an extracranial filter with a filter component having a filter hole array.

It is an object of the invention to provide an additional component including a pressure control, backflow control, a pressure measurement device, a flow measurement device, or combinations thereof.

It is an object of the invention to provide a flow meter that is a sensor suitable for placement under the skin of a human or animal.

It is an object of the invention to provide a sensor that has two chambers, each chamber containing a capacitor and inductor, with each capacitor connected to its comparable inductor in a resonant circuit, and both chambers containing inlets and outlets for the passage of fluid to be measured.

It is an object of the invention to provide a sensor that measures the deformation of a pair of flexible capacitor plates connected by a serpentine channel as a means of converting flow rate of a fluid or gas into a change in capacitance.

It is an object of the invention to provide a sensor that is insensitive to temperature variations and can be immersed in a liquid, gas, or body system.

It is an object of the invention to provide a sensor that uses wireless electronics.

DESCRIPTION OF THE PREFERRED EMBODIMENTS

Figure 1:
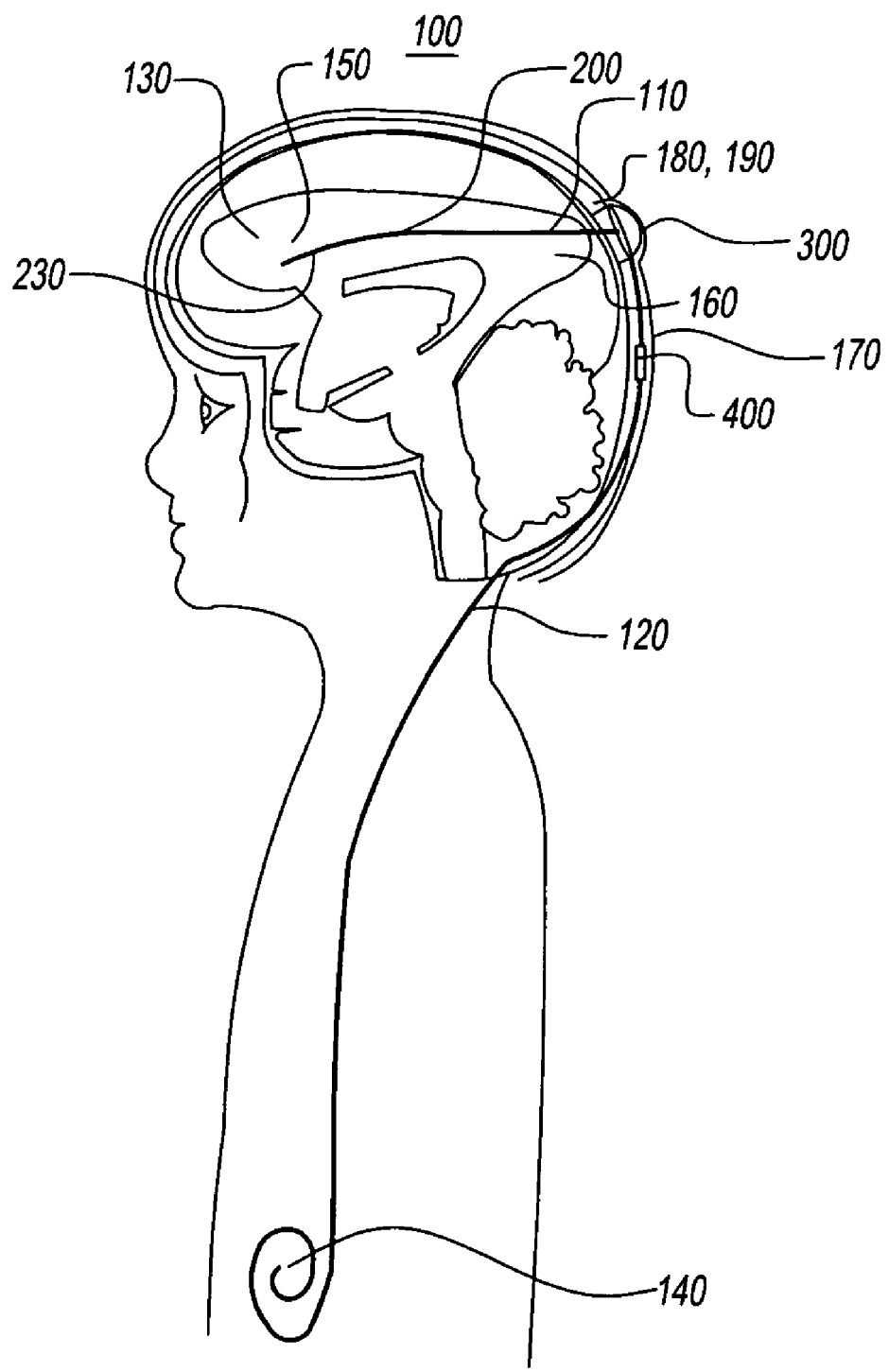
FIG. 1 is a side view of the invention deployed in a human.

FIG. 1 shows medical apparatus 100, with shunt 110, shunt tube 120, shunt proximate end 130, shunt distal end 140, organ 150, skull 160, skin 170, extracranial space 180, subcutaneous space 190, catheter 200, catheter tip 230, extracranial filter 300, additional component 400. The organ may be any organ that requires fluid control, but in a preferred embodiment the organ is a brain or an eye, and the fluid being controlled is CSF, or cerebrospinal fluid. The catheter 200 may be a ventricular catheter, and the organ may be a human brain. Alternately, the organ may be a human eye.

FIG. 1 illustrates how the invention may be used to drain CSF from the brain, and how shunts of the prior art have been improved in this invention. The shunt catheter 200 extends from the organ 150 to the outside of the skull 160, where it enters an extracranial filter 300. The extracranial filter 300 lies just under the skin 170, where it is relatively easy to access. The shunt tube 120 then extends to a sensor 450, which monitors and controls the flow. From there, the shunt tube 120 extends into the stomach for drainage. The shunt tube length may be from 2 mm to 2 m, with a preferred length of 1 m. The shunt tube diameter may be from 0.001 mm to 10 cm, with a preferred diameter of 1.3 mm. The shunt tube and catheter may be made from any material, including but not limited to, poly(methyl methacrylate), any implantable material, including but not limited to, polylactic acid, polyglycolic acid, polypropylene, polytetraflouroethylene, or any plastic or composite, or any combination of these materials or any other materials.

Figure 2A:
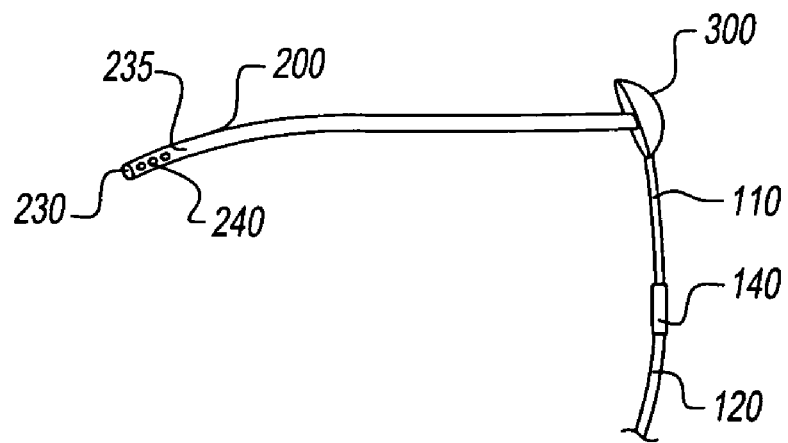
FIG. 2a is a side view of the invention.
Figure 2B:
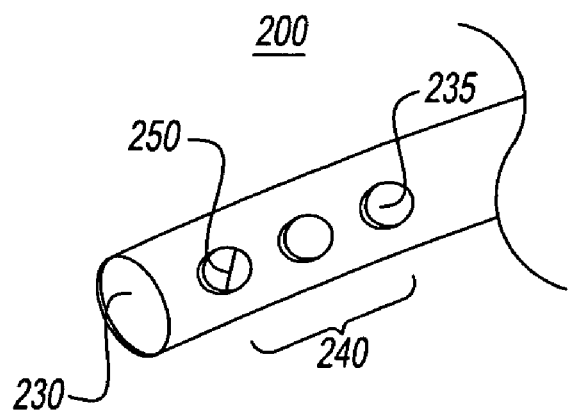
FIG. 2b is an exploded view of the proximate catheter portion of the invention.

FIG. 2a-b show medical apparatus 100, shunt 110, shunt tube 120, catheter 200, catheter tip 230, catheter hole 235, plurality of catheter holes 240, catheter hole diameter 250, and extracranial filter 300.

FIG. 2a illustrates the flow path and components of the invention. FIG. 2b illustrates the catheter 250. In a preferred embodiment, the catheter tip 230 would be open, and the catheter holes 235 would be fewer and larger than in shunt systems of the prior art. The larger catheter holes 235 would make the invention less likely to clog due to particulates or pieces of tissue catching at the catheter tip 230, where they are relatively inaccessible. The catheter hole diameter 250 may be 0.001 mm to 6 mm, with a plurality of holes with a preferred range of diameters being 1.0 mm to 1.3 mm. The catheter holes 235 and catheter tip 230 opening may all be the same size or may be differing sizes. The preferred size of the catheter tip is 1.3 mm inner diameter with 1.3 mm holes in the walls. The holes may be round as shown or may be any other shape, including but not limited to, square, rectangular, pyramidal. There may be any number of holes, from 1 to 50, preferably configured in a close packed array. The particles that pass through the catheter are captured in the extracranial filter 300. The flow rate of the invention is measured and controlled by the additional component 400.

Figure 3A:
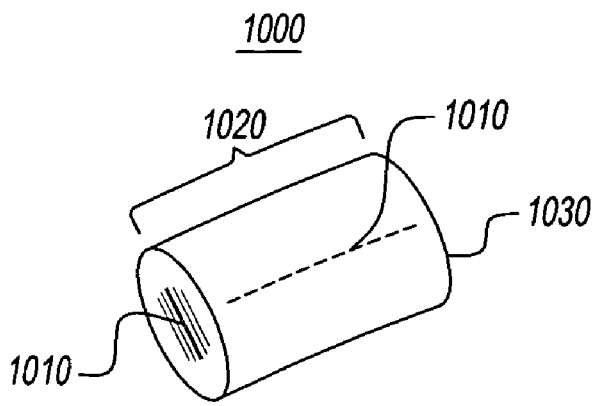
FIG. 3a-c is a side perspective view of the removable sheath of the invention.
Figure 3B:
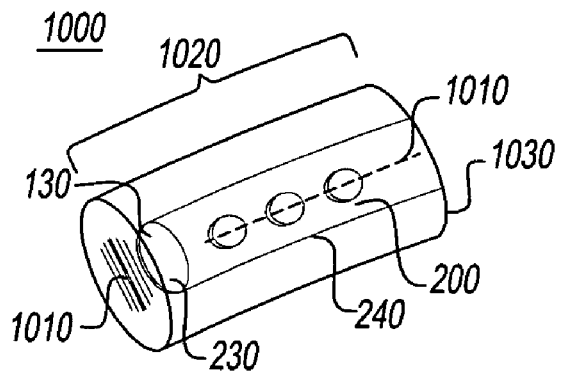
Figure 3C:
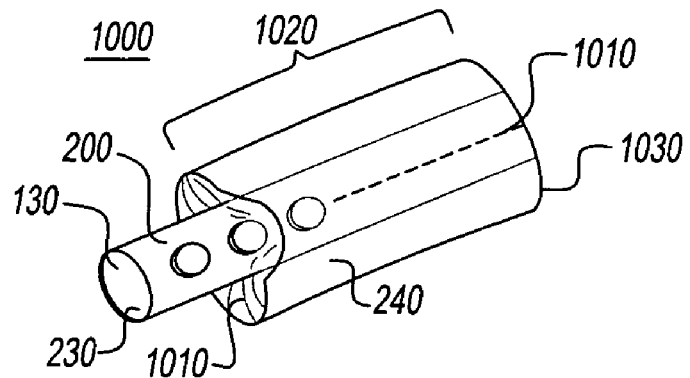

FIG. 3a-c show removable sheath 1000, perforation 1010, tearable seam 1020, removable sheath opening 1030, shunt proximate end 130, catheter 200, and catheter tip 230.

FIG. 3 illustrates how the removable sheath 1000 is used in a patient. FIG. 3a shows the removable sheath 1000 before use. In FIG. 3b, the removable sheath 1000 is slipped over the shunt proximate end 130 to enclose the catheter tip 230 and the plurality of catheter holes 240 in the removable sheath 1000. The shunt is then inserted into a patient. When the shunt is in place and any disturbances are settled, the removable sheath 1000 is pulled away as shown in FIG. 3c, then pulled out of the patient's body through an incision. The removable sheath 1000 rips open at the perforations 1010 and at the tearable seam 1020 to allow ease of removal. The removable sheath could be removed either by tearing perforations at the shunt proximate end 130, by tearing a tearable seam along the length or any portion of the length of the removable sheath, or by any combination of these methods. The number of perforations in the removable sheath may be from 1 to 1000, with a preferred number of 50 and a preferred spacing of 1 mm. Alternately, the removable sheath may have no perforations, and may be removed by cutting or applying other force to remove the removable sheath, for example, like a soda straw. The removable sheath may be constructed of one piece or of multiple pieces.

The removable sheath may be made from any material, including but not limited to, paper and paper products, plastic, cloth, glass or glass products, rubbers, thermoplastics, elastomers, metal, wood or wood products, plasters, or any combination of these or other materials. In a preferred embodiment, the removable sheath is constructed from a thin, waxed paper or a cloth, and would be biocompatible, sterile, and not leave a residue. The sheath need not be coated.

Figure 4:
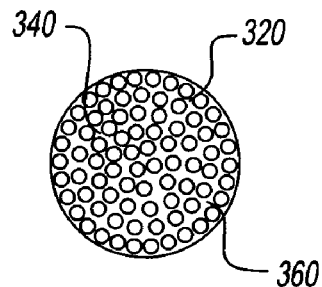
FIG. 4 is a front view of the filter portion of the invention.

FIG. 4 is a front view of extracranial filter 300, with filter pore 320, and in which filter component 360 is shown having a filter component hole array 340. The filter may be a regular array, an irregular array, may consist of one or more layers, or may be fibrous like a filter paper. The filter may be designed such that the fluid flows from top to bottom or from bottom to top. The number of holes in the filter may range from 1 to 1 million, with the preferred number being 10,000. The pore diameter may be from 0.01 mm to 1.3 mm, with a preferred pore diameter of 0.1 mm to 1.3 mm. In one embodiment, the filter has a filter component having a pore size of from about 0.3 mm to 0.4 mm.

The filter resides in a housing that stays in place when the filter is replaced, thus allowing the filter to be replaced with a minimally invasive procedure. The filter and housing may be made from any material, including but not limited to poly(methyl methacrylate), any implantable material, including but not limited to, polylactic acid, polyglycolic acid, polypropylene, polytetraflouroethylene, or any plastic or composite, or any combination of these materials or any other materials.

Figure 5A:
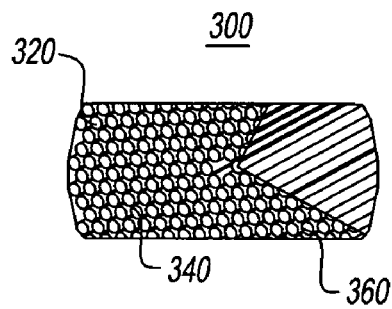
FIG. 5a-b is a cut away view of the filter portion of the invention.
Figure 5B:
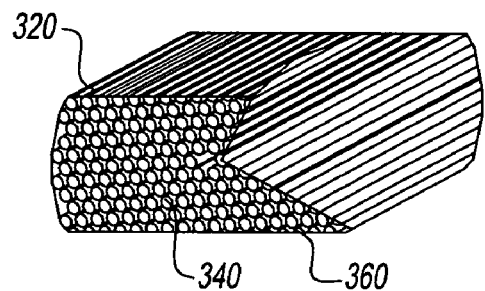

FIG. 5a-b shows extracranial filter 300, filter pore 320, filter component hole array 340, filter component 360. In this figure, one can see that the depth or number of layers in the filter component 360 may encompass a broad range. The depth of the filter component 360 may be from 0.00001 mm to 20 cm, with a preferred depth of 1 mm to 100 mm. The filter housing may any size, with preferred dimensions of 2×3 cm.

Figure 6:
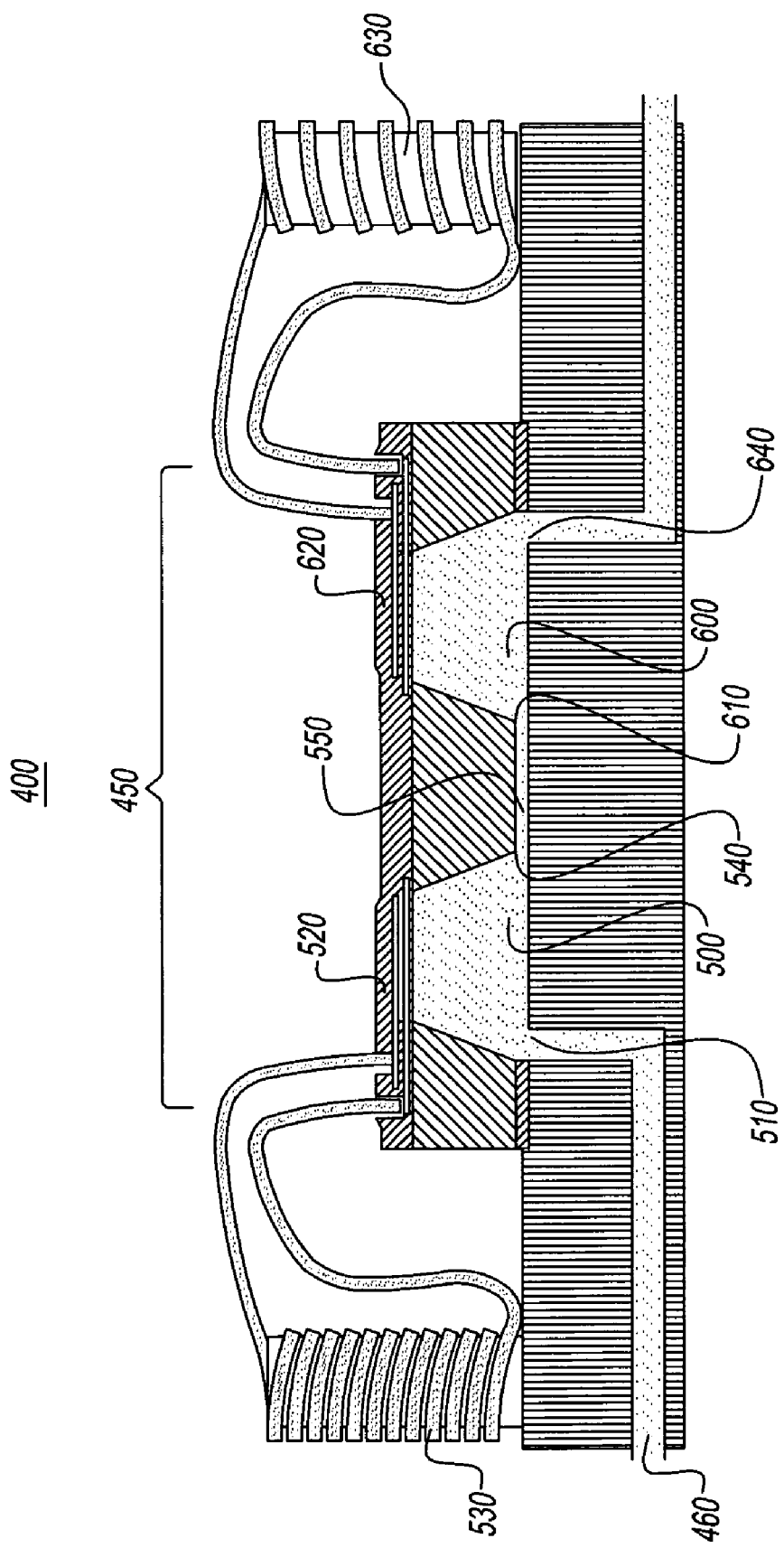
FIG. 6 is a side view of the additional component of the invention.

FIG. 6 shows additional component 400, with sensor 450, fluid 460, sensor first chamber 500, sensor first chamber inlet 510, sensor first capacitor 520, sensor first inductor 530, sensor first chamber outlet 540, channel 550, sensor second chamber 600, sensor second chamber inlet 610, sensor second capacitor 620, sensor second inductor 630, sensor second outlet 640.

The overall dimensions of the sensor 450 may be 1-3 mm in length, 0.1-15 mm in width, and 0.1-15 mm in height, with preferred dimensions of 10 mm long by 5 mm wide by 5 mm high (10 m×5 mm×5 mm). The pressure sensors may be fabricated from any suitable material, with a preferred material being 100 mm silicon wafers with a low stress $SiN_x$ coating, the coating having a thickness of about 0.5 to 1.0 µm. The flexible membrane plate of the capacitor may be made from any material, with a preferred material being a thin film of silicon nitride ($SiN_x$) that is coated with a combination of Cr/Au or Cr/W. The capacitors may have a dimension of ranging from 0.1 to 2 mm², with a preferred dimension of 0.5×0.5 mm². The sensor may be fabricated using any suitable method, including but not limited to anisotropic etching techniques.

Devices to measure pressure wirelessly (and wired) in the low pressure range of biomedical fluids are currently available. Using flow sensors as in the present invention is novel, as is using twin components with a compact serpentine drag channel and wireless read-out.

In a preferred embodiment, the additional component in FIG. 6 can be used to measure fluid flow rate in the medical apparatus 100 by measuring a pressure differential. It is a well known phenomenon that a fluid flowing through a pipe losses pressure due to friction with the wall of the pipe. The additional component 400 consists of two capacitive pressure sensors in the path of the flowing fluid. The difference in pressure between the two sensors is directly proportional to the flow rate and is given by $$\Delta P = -40.7 \frac{\mu V_F l}{D^4} [\text{Pa}] \quad (1)$$

where µ is the viscosity of the fluid, $V_F$ is the volume flow rate, l is the distance between the two sensors along the path of the flow, and D is the diameter of the tube between the two sensors. Equation (1) applies to laminar flow, which is the case for CSF fluid flow in the shunt.

The arrangement for measuring the differential pressure is shown schematically is FIG. 6. One embodiment of the pressure sensor consists of a parallel plate capacitor where one of the plates is constructed from a flexible membrane that is in contact with the CSF fluid. The membrane is deflected (by the pressure of the fluid) towards the fixed plate of the capacitor. Since the capacitance is inversely proportional to the distance between the plates, the capacitance will increase with increasing CSF pressure. Connecting each capacitor in a closed loop with an inductor and inductively coupling to the circuits externally will enable wireless detection of the capacitances and thereby measurement of the differential pressure and CSF flow. Unlike currently available pressure sensors, the present invention is designed to be insensitive to pressure variations; the design also results in a sensor that is insensitive to temperature variations, both of which are important factors when monitoring flow rates in a living body.

There is a set of acceptable parameters for constructing a flow sensor device whose frequencies are detectable wirelessly. The present invention uses a device fabrication strategy that takes advantage of well established micro-electromechanical systems (MEMS) process technology.

The practical implementation of the present invention depends on using the appropriate combination of geometrical and material parameters to give reasonable sensitivity and accuracy under the conditions needed for CSF flow diagnostics. The important conditions are that the flow rate may vary between 20 mL/Hr and 100 mL/Hr while the fluid pressure may very between 200 Pa and 1800 Pa. These conditions were derived from the specifications of currently available shunt devices. The flexible membrane capacitor plate must be sensitive within this range of pressures while the pressure drop, ΔP, between the two capacitors must be large enough to measure CSF flow in the required range with reasonable accuracy. Along with this these requirements, the device LC circuits and the external detection circuit must be designed to give an acceptable detectability within the range of pressures and flow rates.

The deflection of the flexible capacitor plate can be derived from a consideration of the deflection of a thin flexible membrane under a uniform pressure. For a square membrane supported on all sides, the relationship between the pressure, P, and the deflection (at the center of the membrane), w, is given by:[i]

$$P = \frac{c_1 \sigma_0 t w}{a^2} + \frac{c_2 E t w^3}{a^4 (1-v)} \quad (2)$$

where $c_1$=3.393, $C_2$=8/6(1+v), t is the membrane thickness, a is the half-width, $\sigma_0$ is the initial stress of the membrane, E is Young's modulus and v is Poisson's ratio. The current invention uses a capacitor that has 2a=0.5 mm with an air gap, d, of ~1.0 micrometer. The flexible membrane plate of the capacitor is made from a thin film of silicon nitride ($SiN_x$) that is coated with a combination of Cr/Au or Cr/W. The $SiN_x$ membrane would be ~0.5 µm thick. Using E=220 MPa, v=0.28 and $\sigma_0$=100 to 400 MPa for $SiN_x$ and assuming that $SiN_x$ will dominate the membrane mechanical behavior (a reasonable assumption if the metal stack is kept to a minimal thickness), the first term in Eq. 2 dominates P and the deflection, w, is then a linear function of the pressure. With these conditions, the capacitance, $C=4\epsilon_0 a^2/d$, at P=0 is 2.2 pF. The capacitance with the membrane deflected under pressure can be approximated by $$C(w) = \frac{4\varepsilon_0 a^2}{d}\left[1 + \frac{w}{2d}\right] = \frac{4\varepsilon_0 a^2}{d}\left[1 + \frac{a^2 P}{2dc_1\sigma_0 t}\right]. \quad (3)$$

By solving Eq. 3 for P and using Eq. 1 the fluid flow rate is derived from a measurement of the capacitances of the two pressure sensors and is $$V_F = \frac{(C_1 - C_2)d^2 c_1 \sigma_0 t D^4}{162.8\mu l \varepsilon_0 a^4} = B \cdot (C_1 - C_2) \quad (4)$$

where the material properties, geometrical parameters, and physical constants have been grouped into the parameter B. Also, Eq. 4 is valid when the capacitors ($C_1$ and $C_2$) have identical materials and geometry. The present invention detects the capacitances of the two pressure sensors by connecting each in a closed loop with an inductor and finding the resonant frequency of each circuit, which is given by $$f = \frac{1}{2\pi\sqrt{LC}}. \quad (5)$$

Substituting into Eq. 4 the flow rate is expressed as a function of the measured resonant frequencies of the two LC circuits, $$V_F = \frac{B}{4\pi^2}\left[\frac{1}{L_1 f_1^2} - \frac{1}{L_2 f_2^2}\right]. \quad (6)$$

With Eq. 6 the sensitivity of the measured frequency $f_2$ can be calculated as a function of $V_F$. Plotted in FIG. 2 is the change in $f_2$ for a 1 mL/Hr change in $V_F$ using the parameters is Table 1. The resonant frequency of $f_2$~3.5 MHz at $V_F$=0.

TABLE 1

| Parameter | Description | Value | Unit |
|---|---|---|---|
| a | Half-width of capacitor plates ($C_1$, $C_2$) | 0.25 | mm |
| t | SiN$x$ Membrane Thickness | 0.5 | micrometers |
| d | Initial spacing between capacitor plates | 1 | micrometers |
| $\sigma_0$ | Initial membrane stress | $250 \times 10^6$ | Pascal |
| $\epsilon_0$ | Permittivity of free space | $8.85 \times 10^{-12}$ | MKS |
| $c_1$ | Dimensionless parameter | 3.393 | |
| $L_1$ | Inductance of $1^{st}$ pressure sensor coil | 0.001 | henry |
| $L_2$ | Inductance of $2^{nd}$ pressure sensor coil | 0.00095 | henry |
| $\mu$ | Viscosity of water | .0007 | |
| l | Length of channel between sensors | 20 | mm |
| D | Diameter of channel | 0.5 | mm |

The flow sensor is designed to be implanted, with the device being located under skin of the patient with approximately 1 mm to 2 mm of tissue between the sensor and the outer surface of the skin. The separating tissue is conductive and will introduce a loss to the signal detection that is frequency dependent. Technology exists for mitigating this complication and has been implemented in prior applications using wireless detection strategies for medical devices implanted deep within the body. Since the current invention will be implanted close to the skin of the patient, this parasitic loss poses only a minimal risk to the detection strategy.

To maintain the sensitivity the resistance of the LC circuits must be engineered to minimize losses so that an acceptable quality factor can be achieved. An alternative embodiment that meets this condition follows: Variable capacitors $C_1$ and $C_2$ are pressure sensors. $L_{S1}$ and $L_{S2}$ are inductors used the set the resonant frequencies of the sensor loops and are constructed in a toroidal configuration with a magnetic core. $L_P$ which is much less than $L_{S1}$ and $L_{S2}$ is a small coil (pickup or antenna) whose purpose is to couple wirelessly to the external detection circuit. The configuration of sensor inductors ($L_{S1}$, $L_{S2}$ and $L_P$) minimizes parasitic inductive coupling between the detection and sensor circuits that can erroneously shift the resonant frequencies of the sensor circuit. $R_S$ is the residual resistance in the sensor circuits that arises from wiring. In this simplified scheme detection of the resonant frequencies of the sensor circuits is achieved by sweeping the frequency with $V_0$ and transmitting that signal through the antenna $L_D$ which can be a coil. When the frequency in the detection circuit is equal to the resonant frequency of the either of sensor loops the detection circuit will experience a reverse current, which will be detected as a minimum in the voltage $V_D$ across the resistor $R_D$. This is a very simplified version of the detection circuit. In the actual circuit a transimpedance amplifier module would be used instead of $R_D$ to extract the reverse current signal and phase sensitive detection may be employed to track the resonant frequencies in real time.

As is illustrated in the figures, the present invention is a multi-component medical apparatus that solves problems that have not been addressed in the prior art.

Although this invention has been described with a certain degree of particularity, it is to be understood that the present disclosure has been made only by way of illustration and that numerous changes in the details of construction and arrangement of parts may be resorted to without departing from the spirit and the scope of the invention.

We claim:

1. A medical apparatus, comprising:
    a ventricular catheter having a tip and a plurality of holes disposed along the wall of the catheter;
    a removable sheath, configured to enclose the tip of said ventricular catheter and enclose said holes during and after insertion of the ventricular catheter into a human brain, preventing drainage via said holes until said sheath is removed and does not enclose said holes.

2. The medical apparatus of claim 1, wherein the removable sheath is plastic.

3. The medical apparatus of claim 1, wherein the removable sheath is paper or cloth or fiberglass.

4. The medical apparatus of claim 1, wherein the removable sheath is removed by tearing the sheath after insertion.

5. The medical apparatus of claim 4, wherein the removable sheath has at least one perforation.

6. The medical apparatus of claim 4, wherein the removable sheath has a tearable seam.

7. The medical apparatus of claim 4, wherein the ventricular catheter has a tip and a plurality of holes disposed on the catheter, and the sheath covers the tip and plurality of holes during insertion.

8. A medical apparatus, comprising:
    a catheter having a tip and a plurality of holes disposed along the wall of the catheter;
    a removable sheath, configured to enclose the tip of said catheter and enclose said holes during and after insertion of said catheter into a human eye, preventing drainage via said holes until said sheath is removed and does not enclose said holes.

9. The medical apparatus of claim 8, wherein the removable sheath is plastic.

10. The medical apparatus of claim 8, wherein the removable sheath is paper or cloth or fiberglass.

11. The medical apparatus of claim 8, wherein the removable sheath is removed by tearing the sheath after insertion.

12. The medical apparatus of claim 11, wherein the removable sheath has at least one perforation.

13. The medical apparatus of claim 11, wherein the removable sheath has a tearable seam.

14. The medical apparatus of claim 11, wherein the catheter has a tip and a plurality of holes disposed on the catheter, and the sheath covers the tip and plurality of holes during insertion.

* * * * *